(12) United States Patent
Mandelis et al.

(10) Patent No.: US 6,584,341 B1
(45) Date of Patent: Jun. 24, 2003

(54) METHOD AND APPARATUS FOR DETECTION OF DEFECTS IN TEETH

(76) Inventors: Andreas Mandelis, 3 Scarborough Heights Blvd., Scarborough Ontario (CA), M1M 2V3; Stephen H. Abrams, 748 Briar Hill Ave., Toronto Ontario (CA), M6B 1L3; Lena Nicolaides, 2-D Edgewood Ave., Toronto Ontario (CA), M4L 3G7; Jose Agustin Garcia-Hecules, 14 Blakely Ave., Toronto Ontario (CA), M6N 3Y5

( * ) Notice: Subject to any disclaimer, the term of this patent is extended or adjusted under 35 U.S.C. 154(b) by 72 days.

(21) Appl. No.: 09/628,812

(22) Filed: Jul. 28, 2000

(51) Int. Cl.[7] ................................. A61B 6/00
(52) U.S. Cl. .................... 600/476; 600/477; 433/29; 433/37; 433/68
(58) Field of Search .................... 433/29, 215, 12, 433/25, 37, 68; 356/317, 318, 341; 600/473, 476, 477

(56) References Cited

U.S. PATENT DOCUMENTS

| | | | |
|---|---|---|---|
| 4,290,433 A | | 9/1981 | Alfano |
| 5,281,141 A | | 1/1994 | Kowalyk |
| 5,306,144 A | | 4/1994 | Hibst et al. |
| 5,456,603 A | | 10/1995 | Kowalyk et al. |
| 5,616,141 A | | 4/1997 | Cipolla |
| 5,621,745 A | | 4/1997 | Yessik et al. |
| 5,880,826 A | * | 3/1999 | Jung et al. .................... 356/73 |
| 5,885,082 A | | 3/1999 | Levy |
| 6,024,562 A | | 2/2000 | Hibst et al. |

OTHER PUBLICATIONS

"Clinical Applications of New Advances in Occlusal Caries Diagnosis", Milicich, Graeme, *New Zealand Dental Journal*, 96: 23–26: 2000.

* cited by examiner

*Primary Examiner*—Marvin M. Lateef
*Assistant Examiner*—Jeoyuh Lin

(57) ABSTRACT

There is provided a metrologic methodology and instrument, useful for a high-spatial-resolution dynamic diagnostic metrology and instrument, which can provide simultaneous measurements of laser-induced frequency-domain infrared photothermal radiometry (FD-PTR) and alternating-current (ac) modulated luminescence (FD-LM) signals from defects and caries in teeth intraorally. The combination of the luminescence and radiometric frequency scan techniques for inspection of defects and caries in teeth involves irradiating the tooth with a modulated (direct-current (dc) to 100 kHz) excitation source (laser) emitting in the near-ultraviolet, visible, or near-infrared spectral range, generating blackbody Planck-radiation (infrared radiometry) and ac luminescence, and comparing the obtained (amplitude and phase) luminescence and radiometric signals to those obtained from a well characterized sample (reference) to provide the clinician with numerical information on the status of a tooth. The method and device is used to scan teeth intraorally to detect caries and classify caries or the integrity of the enamel or cementum surface, classify the health and integrity of the enamel at the base of occlusal fissures, classify the health and integrity of enamel or cementum surface of the tooth and defects around the margins of restorations, locate the presence of cracks on the enamel or cementum surface, and locate and characterize cracks in dentin on prepared teeth.

17 Claims, 5 Drawing Sheets a) Luminescence b) Photothermal Amplitude c) Photothermal Phase d) Photothermal Amplitude - Sliced

METHOD AND APPARATUS FOR DETECTION OF DEFECTS IN TEETH

FIELD OF INVENTION

The present invention relates to a metrologic methodology and instrumentation, in particular to laser-frequency-domain infrared photothermal radiometry (henceforth referred to as FD-PTR or simply PTR) and frequency-domain luminescence (henceforth referred to FD-LM, or simply LM), for detection of dental defects and caries intraorally.

BACKGROUND OF THE INVENTION

In recent years rapidly increasing research activities have been reported centered on laser induced dc luminescence generated by a continuously (uninterrupted) illuminating optical source as a probing technique for the detection and quantification of physical and chemical processes associated with carious dental enamel. In general, dc luminescence suffers from low signal levels and thus in most cases dyes are used to enhance sensitivity [V. D. Rijke and J. J ten Bosch, "Optical quantification of caries like lesions in vitro by use of fluorescent dye", J. Dent. Res. 69, 1184–1187 (1990)]. Under laboratory conditions, the results appear satisfactory, yet the use of dyes makes the method difficult for clinical applications. Another promising approach is laser-scanned dc fluorescence (or dc luminescence). This technique can detect early carious lesions [J. Baron, K. Zakariasen and B. Patton, "Detecting $CO_2$ laser effects by 3D image scanned laser fluorescence", J. Dent. Res. 72, special issue #1060, 236 (1993);] by producing surface images which are subsequently enhanced via a standard image processing techniques [C. D. Gonzalez, K. Zakariasen, D. N. Dederich and R. J. Pruhs, "Potential preventive and therapeutic hard tissue applications of $CO_2$ and Nd:YAG and Argon lasers in dentistry: A review", J. Dent. Child May–June, 196–207 (1996)]. Nevertheless, the relatively low SNR limits the contrast and the diagnostic ability of dc laser fluorescence.

There have been three patents issued directed to methods involving dc laser luminescence. (R. R. Alfano, U.S. Pat. No. 4,290,433, Sep. 22, 1981; R. Hibst et. al., U.S. Pat. No. 5,306,144, Apr. 26, 1994; R. Hibst et. al. U.S. Pat. No. 6,024,562, Feb. 15, 2000). The last of these patents makes reference to using periodically modulated (chopped) radiation as a means to eliminating ("quasi-filtering out") the background environmental light interference from the illuminated tooth. A suitable chopping frequency is advised, so as not to coincide with the power-line oscillation frequency. It should be noted that the idea of background light-filtering through modulation described in the patent by R. Hibst et al., neither in spirit, nor in practice does it lead those skilled in the art to our method of providing frequency-scanned amplitude and phase signals of modulated (ac) luminescence as a dental diagnostic means in their own right, where the frequency behavior of the LM signal is used to deduce dynamic optical and photothermal properties of the irradiated region, including scanning imaging.

The technique disclosed in U.S. Pat. No. 5,306,144 issued to R. Hibst et. al., and U.S. Pat. No. 6,024,562 issued to R. Hibst et. al. relies upon long lived fluorescence present in carious regions of the tooth that only emits in the red spectral region. This decay time and spectral characteristics are typical of metal free porphyrin monomers (Konig, K., Schneckenburger, H., Hibst, R., "Time-gated in vivo autofluorescence imaging of dental caries", Cell Mol. Biol., 1999, March, Volume 45, #2, pages 233–239). The spectral characteristics were found to be typical of protoporphyrin IX, which may be present due to bacterial biosynthesis occurring within carious tissue (Konig, K., Flemming, G., Hibst, K., "Laser—induced autofluorescence spectroscopy of dental caries", Cell Mol. Biol., 1998, December, Volume 44, #8, pages 1293–1300). There is also speculation that pigments present in specific foods or drink may be responsible (Longbottom, C., "Caries detection—Current status and future prospects using lasers", in Lasers in Dentistry VI, Featherstone, J. D. B., Rechmann, P., Fried, D., Proceedings of SPIE, 2000, Volume 3910, pages 212–218). This is a much different approach to finding carious regions than the invention disclosed in the present patent.

A variety of methods have been developed for using lasers to treat carious tooth structures. Yessik et al. (U.S. Pat. No. 5,621,745 Apr. 15, 1997) describes one method of using a modulated pulsed laser to remove carious tooth material. Kowalyk (U.S. Pat. No. 5,281,141, Jan. 25, 1994) describes a method for using a Nd:YAG laser to treat and remove carious tooth material.

A number of laser systems have been proposed for curing or setting composite resins that are used to directly restore teeth. These resins are placed into cavity preparations that encompass the defects in the tooth or the carious regions of the tooth. Kowalyk (U.S. Pat. No. 5,281,141, January 1994), Kowalyk et al. (U.S. Pat. No. 5,456,603, October 1995), Levy (U.S. Pat. No. 5,885,082 March 1999) and Cipolla (U.S. Pat. No. 5,616,141 April 1997) disclose several techniques for curing or acting as a catalyst for the curing of light cured or dual cured dental composites. Issues such as polymerization shrinkage of the composite resin from the cavity or tooth walls are still being examined (Cobb, D S., et al. "Physical properties of composite cured with conventional or argon laser", Am. J., 1996, October, Volume 9, No. 5, pages 199–202), (Tarle et al. "The effect of photopolymerization method on the quality of resin samples", J. Oral Rehabil., 1998, June, Volume 25, No. 6, pages 436–442). Laser systems may be utilized in the photopolymerization of composites, but heat generation and marginal integrity of the restoration still need to be examined.

Frequency-Domain Photothermal Radiometry (FD-PTR) is a growing technology for the nondestructive evaluation (NDE) of sub-surface features in opaque materials [M. Munidasa, T. C., A. Mandelis, S. K. Brown, and L. Mannik, "Non-destructive depth profiling of laser processed Zr-2.5Nb alloy by infrared photothermal radiometry", J. Mat. Sci. Eng. A 159, 111–118 (1992), G. Walther, "Photothermal nondestructive evaluation of materials with thermal waves" in Progress in photothermal and photoacoustic science and technology, A. Mandelis, ed., Vol. 1, pp. 205–298 Elsevier, N.Y. (1992)]. It has also shown promise in the study of excited-state dynamics in active optically transparent solid-state (laser) materials [A. Mandelis, M. Munidasa, and A. Othonos, "Single-ended infrared photothermal radiometric measurements of quantum efficiency and metastable lifetime in solid-state laser materials: the case of ruby $(Cr^{3+}:Al_2O_3)$", IEEE J. Quant. Electron. 29, 1498–1504 (1993)].

The FD-PTR technique is based on the modulated thermal infrared (blackbody or Planck-radiation) response of a medium, resulting from radiation absorption, non-radiative energy conversion and excited-to-ground-state relaxation, followed by temperature rise and subsequent emission of infrared photons. The generated signals carry sub-surface information in the form of a temperature depth integral. As a result, PTR has the ability to penetrate and yield depth-profilometric information about an opaque medium well below the range of optical imaging. Owing to this ability, pulsed-laser PTR has been extensively used with turbid media such as tissue [A. J. Welch and M. J. C. van Gemert eds., in *Optical-thermal response of laser-irradiated tissue*, Plenum, N.Y (1995), S. A. Prahl, A. I. Vitkin, U. Bruggemann, B. C. Wilson, and R. R. Anderson "Determination of optical properties of turbid media using pulsed photothermal radiometry", Phys. Med. Biol. 37, 1203–1217 (1992)] to study the sub-surface deposition localization of laser radiation, a task which is difficult or impossible for optical methods in tissue due to excessive scattering.

Very recently, dental applications of pulsed PTR focused on the diagnostics of dentin and enamel have been reported as disclosed in D. Fried, W. Seka, R. E Glena, and J. D. B. Featherstone, "Thermal response of hard dental tissues to 9- through 11-$\mu$m $CO_2$-laser irradiation", Opt. Eng. 35, 1976–1984 (1996), D. Fried, S. R. Visuri, J. D. B. Featherstone, J. T. Walsh, W. Seka, R. E. Glena, S. M. McCormack, and H. A. Wigdor, "Infrared radiometry of dental enamel during Er:YAG and Er:YSGG laser irradiation", J. Biomed. Opt. 1, 455–465 (1996). These preliminary studies have examined the temperature behavior of dental tissues, their tolerance to optical-to-thermal energy conversion and deposition, and their ablation threshold by high-fluence pulsed lasers. Unfortunately, the high-fluence deposition and wideband nature of pulsed photothermal detection, coupled with laser-pulse jitter and the high noise content inherent to all broadband thermal (incoherent) signal techniques, prohibits the non-destructive application of this PTR mode to dental imaging, at least in competition with dc luminescence and other imaging diagnostics.

In contrast, FD-PTR, on the other hand, exhibits much higher signal-to-noise ratio (SNR) than its pulsed counterpart [A. Mandelis, "Signal-to-noise ratios in lock-in amplifier synchronous detection: A generalized communications systems approach with application to frequency-, time-, and hybrid (rate-window) photothermal measurements", Rev. Sci. Instrum. 65, 3309–3323 (1994)] and a fixed probed depth with the use of a single modulation frequency. Therefore, it would be very advantageous to provide a method of dental imaging based on FD-PTR.

SUMMARY OF THE INVENTION

The present invention provides a method with frequency-domain infrared photothermal radiometry (FD-PTR) and modulated laser luminescence (FD-LM), as complementary dynamic dental diagnostic tools, for quantifying sound and defective (cracked, carious) teeth intraorally.

In one aspect of the invention there is provided a photothermal radiometric and luminescence method for inspection of teeth, comprising the steps of:

irradiating a portion of a surface of a tooth with a light source emitting at an effective wavelength wherein photothermal radiometric signals and luminescence signals are responsively emitted from said portion of the tooth;

detecting said emitted photothermal signals and said luminescence signals;

demodulating said emitted photothermal signals into photothermal phase and amplitude components and said luminescence signals into luminescence phase and amplitude signals; and comparing said photothermal phase and amplitude signals to photothermal phase and amplitude signals of a reference sample and comparing said luminescence phase and amplitude signals to luminescence phase and amplitude signals of a reference sample to determine differences between said portion of said tooth and said reference sample and correlating said differences with defects in said tooth.

The present invention also provides a simultaneous photothermal radiometric and luminescence method for imaging of a tooth surface and detection of the tooth defects intraorally, comprising the steps of:

scanning a tooth surface intraorally by irradiating the tooth surface with a light source at fixed frequency wherein a photothermal radiometric signals and luminescence signal is responsively emitted from said tooth;

detecting said emitted photothermal radiometric signals and said luminescence signals;

demodulating said emitted photothermal radiometric signals into photothermal phase and amplitude signals and said luminescence signals into luminescence phase and amplitude signals using a lock-in amplifier and normalizing said demodulated photothermal phase and amplitude signals and normalizing said demodulated luminescence phase and amplitude signals to cancel light source fluctuations and lock-in amplifier dependencies; and comparing said normalized photothermal phase and normalized amplitude signals to photothermal phase and amplitude signals of a reference sample and comparing said normalized luminescence phase and normalized amplitude signals to luminescence phase and amplitude signals of a reference sample to determine differences between said portion of said tooth and said reference sample thereby identifying defects in said tooth.

In another aspect of the invention there is provided a device for photothermal radiometric and luminescence for inspection of teeth, comprising the steps of:

a light source for irradiating a portion of a surface of a tooth with an effective wavelength wherein photothermal radiometric signals and luminescence signals are responsively emitted from said portion of the tooth;

detection means for detecting said emitted photothermal signals and said luminescence signals;

demodulating means for demodulating said emitted photothermal signals into photothermal phase and amplitude components and said luminescence signals into luminescence phase and amplitude signals; and processing means for comparing said photothermal phase and amplitude signals to photothermal phase and amplitude signals of a reference sample and comparing said luminescence phase and amplitude signals to luminescence phase and amplitude signals of a reference sample to determine differences between said portion of said tooth and said reference sample and correlating said differences with defects in said tooth.

In this aspect of the invention the light source may be a laser emitting in the near-ultraviolet, visible or near-infrared spectral ranges and the demodulation means may be a lock-in amplifier. In this aspect of the invention the device may include a laser for treatment of defects.

BRIEF DESCRIPTION OF THE DRAWINGS

The method and apparatus for diagnosis and treatment of detects in teeth such as cracks and dental caries according to the present invention will now be described by way of example only, reference being had to the accompanying drawings in which:

FIG. 3b) PTR amplitude; FIG. 3c) PTR phase; and FIG. 3d) PTR amplitude with peaks sliced off;

DETAILED DESCRIPTION OF THE INVENTION

Figure 1:
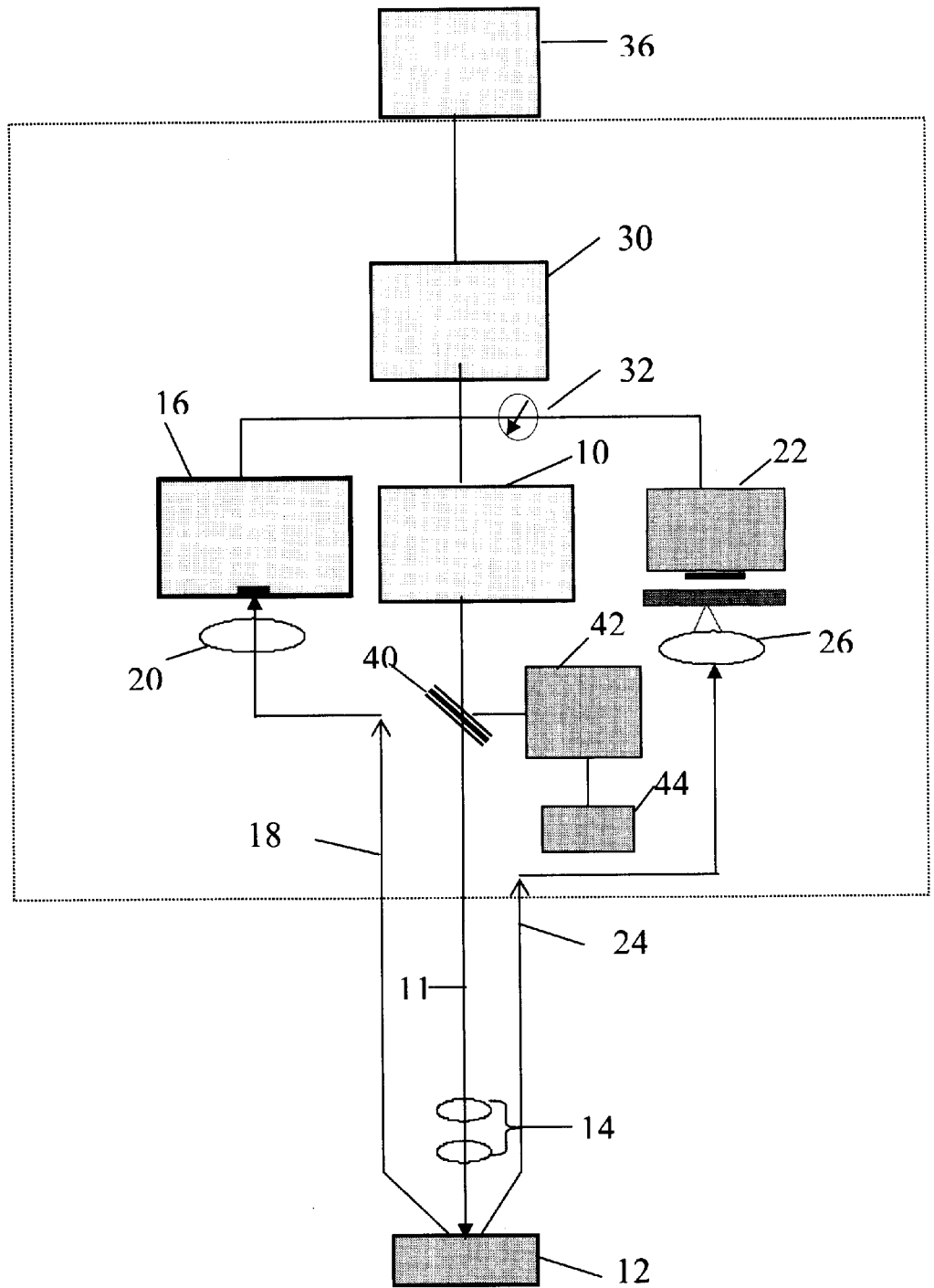
FIG. 1 illustrates a schematic diagram of a first embodiment of a simultaneous frequency-domain infrared photothermal radiometry and frequency-domain luminescence instrument for dental applications according to the present invention.

In the present invention, frequency-domain infrared photothermal radiometry (FD-PTR) and modulated laser luminescence (FD-LM) are coupled to produce complementary coupled dynamic dental diagnostic tools for quantifying cracked and carious enamel. The use of dynamic depth profilometric imaging using simultaneous frequency-domain infrared photothermal radiometry and laser luminescence to study and image cracks and defects in human dental enamel is very advantageous for several reasons. The combination of FD-LM and FD-PTR diagnostic methodologies makes available four signal channels (two amplitudes and two phases) instead of one featured by the state-of-the-art commercial dc luminescence diagnostic methodologies. The correlation of simultaneous data from four channels increases the diagnostic strength of the technique substantially over the current single-signal dc luminescence instruments.

For an image to be formed, either the source or the detector must be localized. Photothermal imaging generally falls into the category of scanned microscopy with a localized source. The current present method is based on low-fluence PTR detection microscopy [L. Nicolaides, M. Munidasa and A. Mandelis, "Thermal-wave diffraction tomographic microscopy", Djordjevic and Reis (eds): *Topics On Non-Destructive Evaluation Series* Vol. 3, pp 65–69 (1998)], which detects the emission of infrared radiation from a heated region of the sample without thermally altering the sample. A temperature oscillation due to modulated heating causes a variation in the thermal emissions, which is monitored using an infrared detector. The temperature modulation allows thermal energy to reach the surface diffusively from a depth approximately equal to a thermal wavelength, $$\lambda_{th}(f)=2\pi\sqrt{\alpha/\pi f}$$

where α is the material thermal diffusivity [cm$^2$/s] and f is the laser beam modulation frequency. Scatterers located within a fraction of a thermal wavelength from the source dominate the contrast of radiometric images. In this way, when the thermal wavelength is varied, e.g. by changing the laser-beam modulation frequency, the region of the specimen that contributes to the image is also varied. In turbid media such as teeth, the signal is controlled by both the optical diffusion (scattering) depth $L_{sc}=1/\mu_{sc}$, where $\mu_{sc}$ is the scattering coefficient [cm$^{-1}$] and the thermal diffusion length, $L_{th}(f)=\lambda_{th}(f)/2\pi$ as disclosed in A. Mandelis, L. Nicolaides, Y. Chen and I. A. Vitkin, "Optical property determination of turbid media using frequency-domain infrared photothermal radiometry, in *Biomedical Optoacoustics*, A. A. Oraevsky, Ed., SPIE vol. 3916, Belligham, Wash., pp. 122–129 (2000).

The basic ingredients of a FD-PTR and/or FD-LM dental microscope are a source of energy, a physical scatterer (the tooth) and a detector of the radiation scattered by the tooth. A convenient source of energy is the laser beam, which can be easily modulated and focused to yield a coherent localized energy source.

A block diagram of an apparatus for inspection of defects and/or caries on samples of dental nature using laser PTR and modulated luminescence as a preferred (but not sole) embodiment of the present invention will now be described with reference to FIG. 1. A heating and luminescence exciting continuous-wave (CW) or pulsed laser 10 of suitable wavelength encompassing, but not restricted to, the ultraviolet (UV) to infrared (IR) spectral range, with modulated intensity (power) in the mW to a few-Watt range, produces a laser beam 11 is directed onto the surface of a tooth 12 using focusing optics 14. The blackbody radiation and luminescence signals emitted by the surface and throughout the bulk of the tooth 12 are collected and focused onto an infrared detector 16 (using an infrared optical fiber bundle 18 and focusing optics 20) and a photodiode detector 22 (using an optical fiber bundle 24 and focusing optics 26), respectively. Exemplary infrared optical fiber technology that may be used includes bundles of silver-halide fibers suitable for thermal imaging as disclosed in E. Rave, D. Shemesh and A. Katzir, "*Thermal imaging through ordered bundles of infrared-transmitting silver-halide fibers*", Appl. Phys. Lett. 76, 1795 (2000). Detector 16 may be a liquid-N$_2$ or thermoelectrically cooled HgCdTe (e.g. EG & G Judson model J15D16-M204) with an active area of 1 mm$^2$ or less and a spectrally sensitive range of 2–10 μm. Other non-cryogenic IR detectors such as pyroelectric sensors or Golay cells may be substituted for the HgCdTe detector, as required. An anti-reflection (AR)-coated Ge window with a transmission bandwidth of 2–13 μm is mounted in front of infrared detector 16 (which includes a pre-amplifier) to block any visible radiation from the pump laser 10. The pump spot diameter of the laser beam 11 on the surface of tooth 12 is typically ca. 30–50 μm. The photothermal signal, which is proportional to the change of the IR radiation emitted from an area viewed by detector 16 is amplified by a preamplifier (not shown) included with the infrared detector (e.g. EG & G Judson model PA-101) before being sent to a digital lock-in amplifier 30 (e.g. Stanford Research Systems, Model SR 850).

The ac luminescence emitted by the tooth 12 is collected with optical fiber bundles and directed to photodetector 22, the output of which is also fed into the same or a different lock-in amplifier 30. A computer controlled or manual switch 32 may be located between the outputs of detectors 16 and 22 sequentially feeding each signal to a single two-phase lock-in amplifier 30 and storing the data in a computer 36. Lock-in amplifier 30 is interfaced with computer 36 so that the frequency scan and data acquisition and storage are automated using suitable software. All these electronics can be compacted and simplified into customized electronics for single or discrete frequency applications or for separate FD-PTR or FD-LM embodiments, as desired. The computer 36 or an equivalent substitute digital readout device will give the clinician a real time reading of the status of the tooth surface and this information can also be stored in the computer for future reference.

An optical reference signal may be obtained using a beam splitter 40 and a silicon photodiode 42 as monitors of the pump laser 10 intensity. A light-emitting-diode (LED) readout 44 can provide the clinician with an indication of the integrity of the laser source and the onset of failure. Alternatively, another embodiment of the invention will use the ratio of the PTR and/or LM amplitude with the photodiode 42 output to keep the signal outputs independent of laser source intensity. Yet another embodiment of the invention will only use the ratio of the PTR and LM signal amplitudes and the difference of their respective phases at two (or more) predetermined modulation frequencies as normalized signals to cancel out all effects of laser source power fluctuation and instrumental frequency dependencies (transfer function). Another embodiment of the invention may use the ratio of PTR and/or LM amplitudes and difference of respective phases from a carious or cracked tooth with that from a healthy location of the same tooth (used as a reference) as determined by the attending dentist.

A further embodiment of the invention involves a step-functional pulse illumination of duration τ in the radiometric experimental set up. This can be used for depth evaluation of the dentin-enamel junction. The step-functional pulse illumination can be generated using a pulse generator to drive the acousto-optic modulator.

Figure 2:
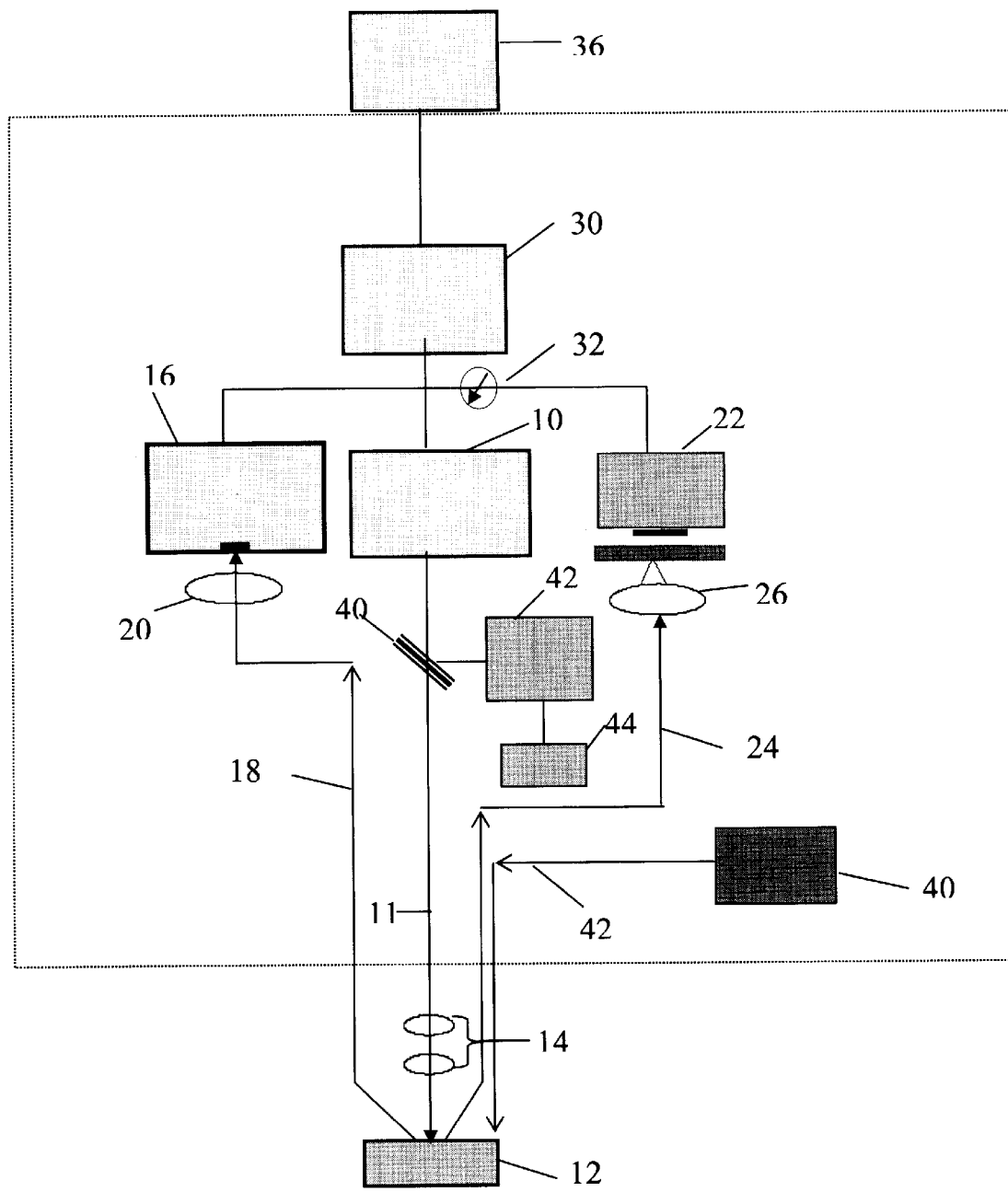
FIG. 2 is a schematic diagram of a second embodiment of a simultaneous frequency-domain infrared photothermal radiometry and frequency-domain luminescence instrument for dental applications constructed in accordance with the present invention for treating and restoring carious teeth.
Figure 3:
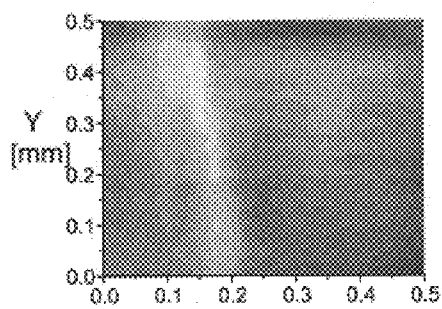
FIGS. 3a to 3d show simultaneous luminescence and FD-PTR images at f=20 Hz in which FIG. 3a) luminescence amplitude.
Figure 3:
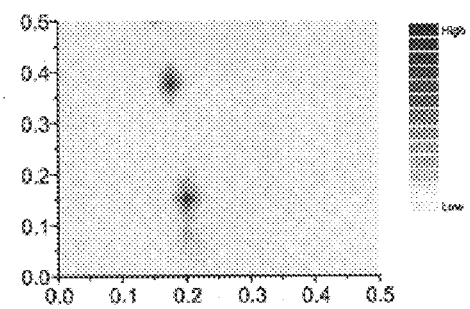
Figure 3:
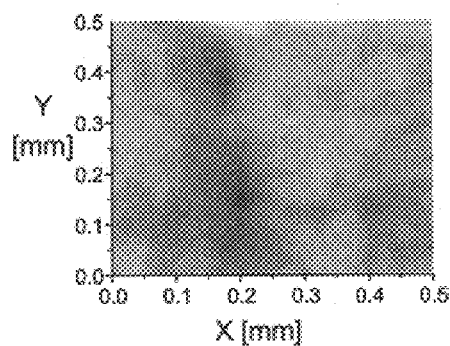
Figure 3:
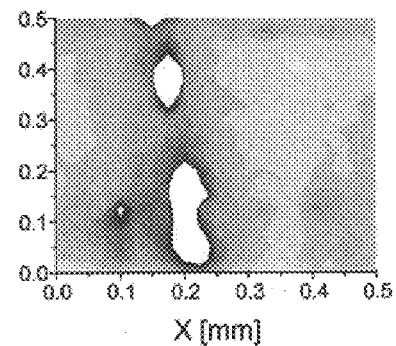

The apparatus shown in FIG. 2 includes all the elements of the apparatus of FIG. 1 and in addition includes a laser 40 (or multiple lasers) emitting in the UV to IR spectral range through optical fiber bundles 42 for the removal of carious tooth material, preparation of the tooth to receive a direct placed restorative material and the curing of a light cured or dual cured composite filling material.

It will be appreciated by those skilled in the art that numerous other configurations for repetitively heating samples and measuring the resulting photothermal radiometric and luminescence signals may be used. The above examples are meant to be non-limiting and illustrative only.

1) Method for Detecting Cracks in Teeth

The apparatus of FIG. 1 has been used to detect sub-surface and near-surface cracks in teeth using scanning imaging of the affected area and setting the modulation frequency to optimally image the cracked region. Ideally, the probing centroid (determined as the weighted mean between the thermal diffusion length $L_{th}(f)$ and the scattering length, $L_{sc}$) must be adjusted so as to be approximately equal to the depth where the sub-surface crack is located. Alternately, frequency scans of the cracked region can be taken and a comparison made with similar scans from a healthy location on the same tooth. Studies by the inventors have shown that the full ac luminescence amplitude range between good and cracked enamel is less than a factor of 2 and the luminescence phase exhibits clear indications of the crack presence in the frequency range above 100 Hz. On the other hand, the FD-PRT amplitude from cracked teeth can increase by as much as 2 orders of magnitude over that from healthy enamel, while the PTR phase exhibits strong changes in shape over the entire dc-100 kHz frequency range.

As an example of the potential of the combined ac techniques in diagnosing dental sub-surface cracks inside the enamel, simultaneous PTR and luminescence images were obtained at different modulation frequencies and in all reported images, the signal ranges between high (black) and low (light gray). A flat enamel slice with a single 15 μm wide transverse crack, 2-mm thick and 6 mm×10 mm in size was imaged at f=20 Hz. The aim was to show the intrinsic features of, and anti-correlation between, PTR and luminescence images.

The results of a 0.5 mm×0.5 mm image of the flat enamel slice with a near vertical sub-surface crack are shown in FIGS. 3a to 3d. The luminescence image shown in FIG. 3a appears to be sensitive to the presence of the crack; in the cracked region the luminescence signal is low (light gray) whereas in the (nearly) intact region the luminescence is relatively high (gray). Within the crack region, luminescence photon emission of several wavelengths characteristic of the enamel chromophores is essentially absent due to the material structural destruction. As a result most of the incident energy decays nonradiatively, yielding a strong photothermal radiometric signal. Conversely, in the intact part of the enamel the luminescence is significantly enhanced, while the photothermal contribution is decreased. The two images together represent the expected balance of excited-state energy release between a radiative (luminescence) and a nonradiative (thermal-decay) dynamic process. The PTR image is the result of thermal-wave generation in the tooth and thus consists of two channels; amplitude and phase, FIGS. 3 (b–d). In turbid media these channels carry thermal transport information within approximately one thermal centroid below the surface. The thermal diffusion centroid is determined as the "center-of-mass" among thermal diffusion length, $\mu_{th}/2\pi$ optical absorption depth and optical scattering mean-free-path in the bulk of the material.

Photothermal amplitude is generally more sensitive to surface property variations, such as the reflectance, whereas phase is largely insensitive to the optical properties of the surface and probes a larger depth range [G. Busse, "Optoacoustic and photothermal inspection techniques", Appl. Opt. 21, 107 (1982)] into the material. In FIG. 3(b) the PTR amplitude exhibits two "hot spots" in the defective enamel. These two spots are also seen in phase, FIG. 3(c), confirming that the extent of these regions of the crack is deeper into the enamel. From optical observation of the tooth after the scan it is estimated that the penetration of the crack spots is 300 μm. The luminescence image shown in FIG. 3(a) however shows the crack damage to be uniform throughout the extend of the crack. This is probably due to the influence of enhanced optical scattering at the crack leading to photon diffusion and "blurring" of the luminescence emission from dental enamel and points to the major difference between the two imaging principles: PTR images depth profiles of sub-surface heat sources; luminescence does not, but is affected by image "blurring" due to photon scattering at the crack. It turns out it is also affected by photon emission delay processes which are characteristic of the material (enamel).

FIGS. 3a to 3d further point to the other major difference between the two techniques: the superior dynamic range of the PTR amplitude. For this reason, the image in FIG. 3(b) is sliced to allow the visualization of other features, the PTR intensity of which is much lower than the peaks of the defect regions. The sliced image is seen in FIG. 3(d), whose features are now comparable to the PTR phase, FIG. 3(c). On the contrary, the luminescence amplitude is essentially continuous along the crack and shows neither the detailed morphology of the cracked region, nor any similarly great signal variations from the surrounding regions.

Studies by the inventors of FD-LM as a diagnostic of dental cracks have shown that FD-LM is a dental imaging method of superior contrast to the conventional dc luminescence, specifically at the enamel-dentin interface. In turn, the depth profilometric character of FD-PTR was found to be superior to that of FD-LM, in terms of defective enamel information obtained at different depths and also in terms of enamel absence and presence of dentin at the enamel-dentin interface. Some degree of depth profilometry has been exhibited by FD-LM, primarily through the depth distribution of the two luminescence decay characteristic relaxation lifetimes (~ms and ~μs) discovered in the behavior of the FD-LM phase, see FIG. 3a. The longer relaxation lifetime appears to be associated with hydroxyapatite and almost never varies, whereas the shorter one varies with laser fluence (a behavior similar to excited-state quenching in optical materials, to which PTR is sensitive) and with the crack density (or the carious state) of the tooth.

2) Method for Detecting Dental Caries and Defects in Teeth

Figure 4A:
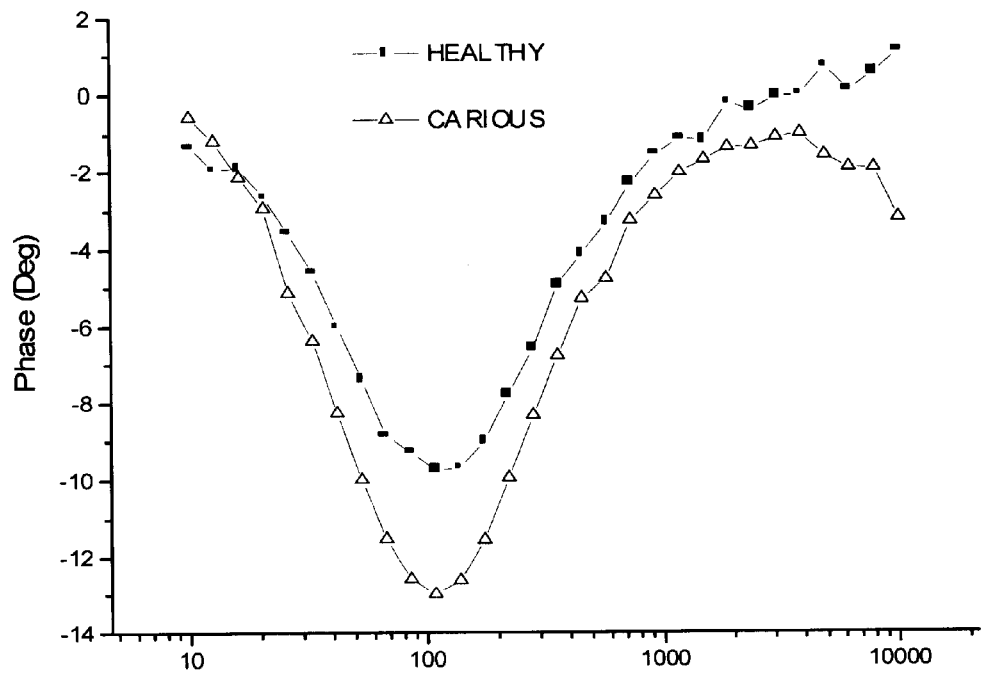
FIGS. 4a and 4b show the phase and amplitude plots respectively of an ac luminescence response in the frequency-domain for a healthy and carious spot on a human tooth in which the excitation source was a 488 nm Argon Ion laser.
Figure 4B:
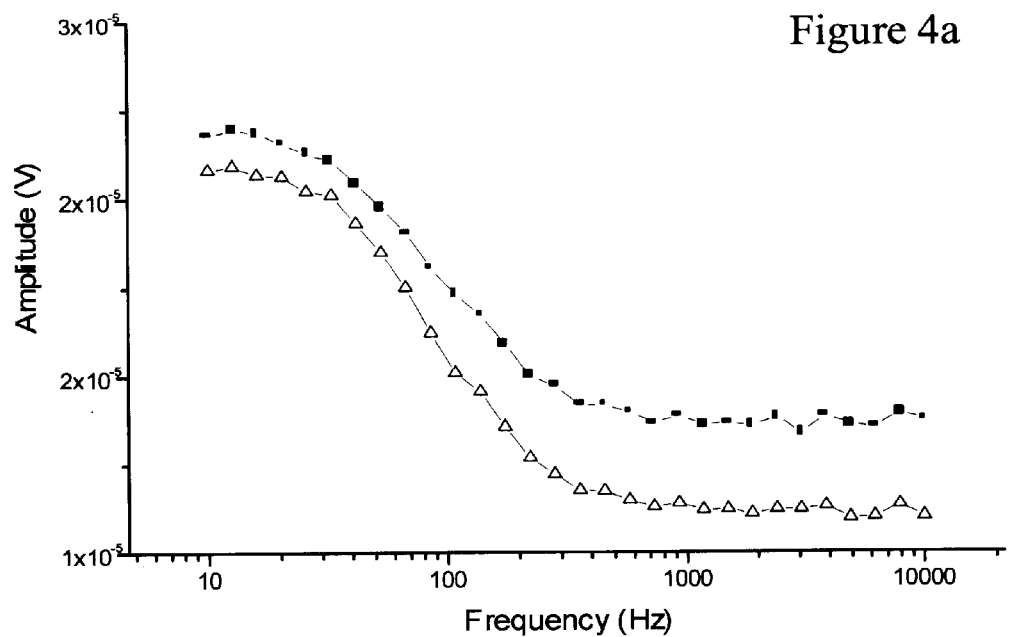

The method of the present invention is based on low-fluence photothermal radiometric detection and modulated luminescence microscopy, which detects the emission of infrared radiation from a heated region of the sample without thermally altering it. A temperature oscillation due to modulated heating causes a variation in the thermal emissions, which is monitored using an infrared detector. The temperature modulation allows for thermal energy to reach the surface diffusively from a depth approximately equal to a thermal wavelength, where α is the material thermal diffusivity [cm²/s] and f is the laser beam modulation frequency. FIGS. 4a and 4b show the phase and amplitude plots respectively of an ac luminescence response in the frequency-domain for a healthy and carious spot on a human tooth in which the excitation source was a 488 nm Argon Ion laser. The effect of caries (demineralization) of a tooth on FD-LM, is to suppress the absolute amplitude throughout the entire frequency range (see FIG. 4b) thus rendering a calibrated relative scale of amplitudes between healthy and carious dental tissue a reasonable measure of the carious state. The FD-LM phase exhibits little differentiation between healthy and carious tissue up to approximately 1 kHz, as observed in the almost equal slopes of the two traces in FIG. 4a. The high-frequency end, however, changes significantly depending on the carious state and can be used for calibration and/or imaging purposes.

Figure 5A:
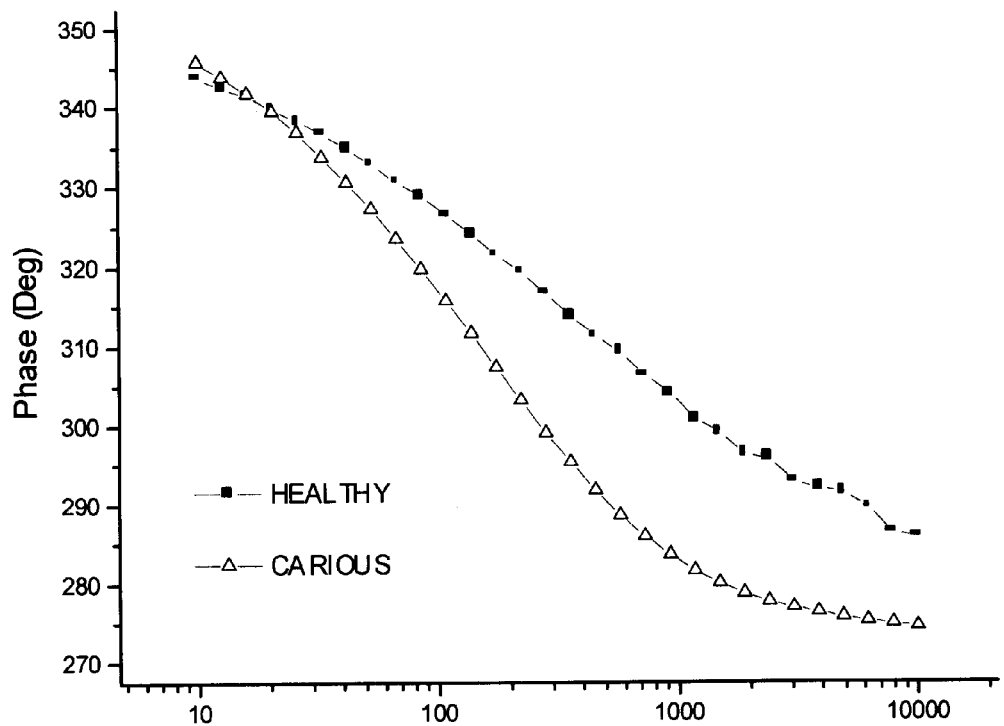
FIGS. 5a and 5b show the phase and amplitude plots respectively of the photothermal response in the frequency-domain for a healthy and carious spot on a human tooth in which the excitation source was 488 nm Argon Ion laser.
Figure 5B:
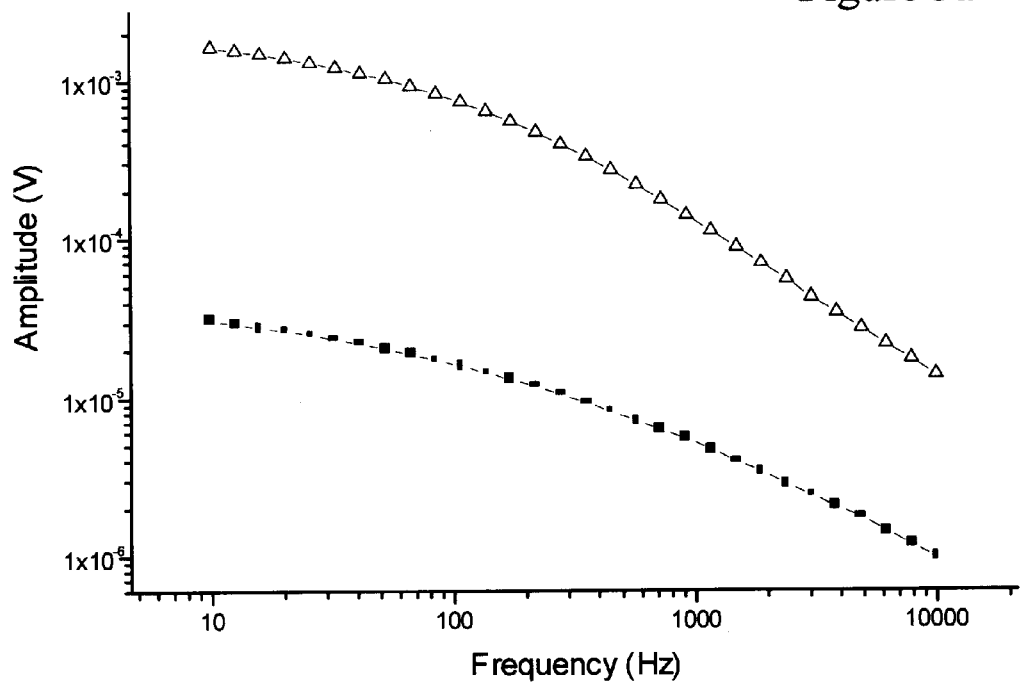

FIGS. 5a and 5b show the phase and amplitude plots respectively of the photothermal response in the frequency-domain for a healthy and carious spot on a human tooth in which the excitation source was 488 nm Argon Ion laser. Here the amplitude of the PTR signal from carious teeth is seen to increase by orders of magnitude compared to healthy dental tissue. Also, the PTR phases between carious and healthy dental tissue vary substantially in shape and absolute value. Furthermore, the PTR phase is, in principle, independent of the emissivity of tooth surfaces, thus comprising an ideal imaging channel of sub-surface caries. These features render PTR into a very sensitive dental caries diagnostic technique, which, when properly calibrated, can yield information.

The amplitude results of FIGS. 4b and 5b show that the radiometric signals at low excitation wavelengths (488–514 nm) are in general anti-correlated with the luminescence signals, as a result of the nature of the two physical signal generation processes. The radiometric signal channel has a much superior dynamic (signal resolution) range that helps distinguish between intact and damaged sub-surface structures in the enamel and dentin. The radiometric signal (amplitude and phase) adds the capability to produce dental images with accurate defect localization, delineation and resolution commensurate with the laser beam size (30–50 μm). The FD-PTR images (amplitude and phase) at a fixed modulation frequency have depth profilometric features. ac luminescence frequency responses from enamel, dentin and hydroxyapatite exhibit two modulated relaxation lifetimes, the longer of which (~ms) is common to all three materials. The luminescence intensity is proportional to the density of luminescence chromophores in the tooth, as well as to their particular location. Therefore, relative FD-LM amplitudes are characteristic of the carious state of a tooth, with the ~μs decay lifetime providing additional information on sub-surface defects, cracks and the onset of caries.

The method and device disclosed herein may be advantageously used for several diagnostic dental applications including: scanning teeth intraorally to detect caries and classify caries or the integrity of the enamel or cementum surface, to classify the health and integrity of the enamel at the base of occlusal fissures, to classify the health and integrity of enamel or cementum surface of the tooth, study defects around the margins of restorations, locate the presence of cracks on the enamel or cementum surface, and locate and characterize cracks in dentin on prepared teeth.

A further variation on the method of the present invention involves combining the diagnostic instrument with another laser in the same instrumentation package to create instrumentation for both the diagnosis of tooth defects and treatment thereof, including preparation of the defective portion of the tooth as well as the curing of various filling materials (e.g. composite resin based filling materials) and the preparation of the tooth surface to receive these materials.

For example, if the data and clinical expertise indicates the presence of pathology, providing the ability to treat the tooth by using lasers that are presently on the market to: remove the decayed or carious tooth material; prepare the tooth using known principles of tooth preparation design; cure or set the light-cured or dual-cured composite material in the tooth preparation restoring the tooth to form and function, using suitable laser-fluence delivery protocols through pulse-waveform engineering, for precise, optimized control of optical radiation delivery and thermal energy generation.

The use of laser-pulse-intensity waveform engineering may be used in the present invention for optimization of the delivery of optical curing radiation and minimization of thermal load effects to the tooth. This may be achieved by means of an optimal duty-cycle program over each laser-beam modulation period, designed to maximize exposure to laser light while minimizing heat generation in the tooth.

In addition, the present method and apparatus may be combined with current technology to create an instrument that will allow the clinician to: diagnose tooth decay, remove carious tooth material and prepare a standard cavity preparation that is of the proper shape and form for a filling material and to etch or roughen the surface of the prepared tooth using a laser, place and cure a light cure or dual cured composite filling material, the placement and curing of a light cured composite or direct placement fissure sealing material.

As mentioned in the Background of The Invention above, a variety of methods have been developed for using lasers to treat carious tooth structures. Yessik et al. (U.S. Pat. No. 5,621,745 Apr. 15, 1997) describes one method of using a modulated pulsed laser to remove carious tooth material. Kowalyk (U.S. Pat. No. 5,281,141, Jan. 25, 1994) describes a method for using a Nd:YAG laser to treat and remove carious tooth material. These methods or possibly another approach using the well-known principle of laser ablation [E. C. Benck, Z. Rong, S. H. Chen, Z. C. Tang and H. A, Schuessler, Appl. Phys. Lett. 58, 1476 (1991); and Appl. Surf. Sci. 48, 257 (1991); R. Srinivasan, B. Braren and R. W. Dreyfus, J. Appl. Phys. 61, 372 (1987); and G. Gorodetsky, T. G. Kazayaka, R. L. Melcher and R. Srinivasan, Appl. Phys. Lett. 46, 828 (1985)] may be combined in with the present apparatus to provide therapeutic tools to the clinician to remove carious tooth material that had been found with the present method.

Therefore, the foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. A photothermal radiometric and luminescence method for inspection of teeth, comprising the steps of:

irradiating a portion of a surface of a tooth with a light source emitting at an effective wavelength wherein photothermal radiometric signals and luminescence signals are responsively emitted from said portion of the tooth;

detecting said emitted photothermal signals and said luminescence signals;

demodulating said emitted photothermal signals into photothermal phase and amplitude components and said luminescence signals into luminescence phase and amplitude signals; and comparing said photothermal phase and amplitude signals to photothermal phase and amplitude signals of a reference sample and comparing said luminescence phase and amplitude signals to luminescence phase and amplitude signals of a reference sample to determine differences between said portion of said tooth and said reference sample and correlating said differences with defects in said tooth.

2. The method according to claim 1 wherein said reference sample is a known healthy portion of a tooth.

3. The method according to claim 2 the step of irradiating includes monitoring an intensity of light from the light source.

4. The method according to claim 3 wherein said step of comparing includes ratioing said photothermal amplitude signals and said luminescence amplitude signals said intensity of the light source to provide photothermal and luminescence amplitude signals independent of light source intensity.

5. The method according to claim 1 wherein said step of comparing includes normalizing said photothermal amplitude signals and said luminescence amplitude signals by ratioing photothermal amplitude signals at least two different frequencies, ratioing luminescence amplitude signals at said at least two different frequencies, and taking a difference of photothermal phase signals at said at least two frequencies and taking a difference of luminescence phase signals at said at least two different frequencies to cancel effects of light source intensity fluctuations and instrumental frequency dependence.

6. The method according to claim 5 wherein said step of demodulating said emitted photothermal signals into photothermal phase and amplitude components and said luminescence signals into luminescence phase and amplitude signals is done using a lock-in amplifier and wherein said instrumental frequency dependence is lock-in amplifier response.

7. The method according to claim 1 wherein said step of demodulating said emitted photothermal signals into photothermal phase and amplitude components and said luminescence signals into luminescence phase and amplitude signals is done using a lock-in amplifier and wherein said instrumental frequency dependence is lock-in amplifier response.

8. The method according to claim 1 wherein said effective wavelength emitted by said light source is in the near-ultraviolet, visible, or near-infrared spectral ranges.

9. The method according to claim 7 wherein said effective wavelength emitted by said light source is in the near-ultraviolet, visible, or near-infrared spectral ranges.

10. The method according to claim 1 wherein said light source is a modulated laser that produces periodic frequency pulses of a laser beam in a range from dc to about 100 kHz.

11. The method according to claim 1 wherein said step of comparing includes generating a baseline signal transfer function, H(f), by obtaining frequency-scan data from said reference sample with known radiometric and dynamic (ac) luminescence properties and frequency response; and comparing said portion of a surface and said known healthy portion of a tooth by means of ratios of photothermal amplitudes, ratios of luminescence amplitudes, and phase differences between photothermal phases and luminescence phases at different frequencies for cancellation of the instrumental frequency response.

12. A simultaneous photothermal radiometric and luminescence method for imaging of a tooth surface and detection of the tooth defects intraorally, comprising the steps of:

scanning a tooth surface intraorally by irradiating the tooth surface with a light source at fixed frequency wherein a photothermal radiometric signals and luminescence signal is responsively emitted from said tooth;

detecting said emitted photothermal radiometric signals and said luminescence signals;

demodulating said emitted photothermal radiometric signals into photothermal phase and amplitude signals and said luminescence signals into luminescence phase and amplitude signals using a lock-in amplifier and normalizing said demodulated photothermal phase and amplitude signals and normalizing said demodulated luminescence phase and amplitude signals to cancel light source fluctuations and lock-in amplifier dependencies; and comparing said normalized photothermal phase and normalized amplitude signals to photothermal phase and amplitude signals of a reference sample and comparing said normalized luminescence phase and normalized amplitude signals to luminescence phase and amplitude signals of a reference sample to determine differences between said portion of said tooth and said reference sample thereby identifying defects in said tooth.

13. The method according to claim 12 wherein upon detecting a defective portion of a tooth such as cracks and fissures in the tooth, carious lesions or decayed portions including treatment of said tooth by;

the preparation of the tooth surface for bonding the material by etching using one of a laser or acid, and curing or initiation of curing of a light cured or dual cured composite resin to restore the defect or carious lesion or to seal the fissure or defect in question.

14. A device for photothermal radiometric and luminescence for inspection of teeth, comprising the steps of:
 a light source for irradiating a portion of a surface of a tooth with an effective wavelength wherein photothermal radiometric signals and luminescence signals are responsively emitted from said portion of the tooth;
 detection means for detecting said emitted photothermal signals and said luminescence signals;
 demodulating means for demodulating said emitted photothermal signals into photothermal phase and amplitude components and said luminescence signals into luminescence phase and amplitude signals; and
 processing means for comparing said photothermal phase and amplitude signals to photothermal phase and amplitude signals of a reference sample and comparing said luminescence phase and amplitude signals to luminescence phase and amplitude signals of a reference sample to determine differences between said portion of said tooth and said reference sample and correlating said differences with defects in said tooth.

15. The device according to claim 14 wherein said light source is a laser emitting in the near-ultraviolet, visible, or near-infrared spectral ranges.

16. The device according to claim 14 wherein said demodulation means is a lock-in amplifier.

17. The device according to claim 14 including a laser for preparation of a defective tooth portion and curing of dental resins.

* * * * *